United States Patent
Mukai et al.

(10) Patent No.: US 10,994,056 B2
(45) Date of Patent: May 4, 2021

(54) DEVICE FOR FIXING BIOLOGICAL SOFT TISSUE, AND METHOD FOR PRODUCING SAME

(71) Applicant: NATIONAL UNIVERSITY CORPORATION KOBE UNIVERSITY, Hyogo (JP)

(72) Inventors: Toshiji Mukai, Hyogo (JP); Naoko Ikeo, Hyogo (JP); Eisei Gu, Hyogo (JP); Takumi Fukumoto, Hyogo (JP); Hikaru Yabuuchi, Hyogo (JP)

(73) Assignee: NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 968 days.

(21) Appl. No.: 15/510,106

(22) PCT Filed: Sep. 9, 2015

(86) PCT No.: PCT/JP2015/004596
§ 371 (c)(1),
(2) Date: Mar. 9, 2017

(87) PCT Pub. No.: WO2016/038892
PCT Pub. Date: Mar. 17, 2016

(65) Prior Publication Data
US 2017/0258968 A1      Sep. 14, 2017

(30) Foreign Application Priority Data

Sep. 9, 2014 (JP) .............................. JP2014-183716
Mar. 12, 2015 (JP) .............................. JP2015-050101

(51) Int. Cl.
*A61L 31/00*       (2006.01)
*C22C 23/04*       (2006.01)
(Continued)

(52) U.S. Cl.
CPC ............ *A61L 31/00* (2013.01); *B21C 23/002* (2013.01); *B22D 7/005* (2013.01); *C22C 1/02* (2013.01);
(Continued)

(58) Field of Classification Search
None
See application file for complete search history.

(56) References Cited

U.S. PATENT DOCUMENTS 8,034,101 B2      10/2011   Yamamoto et al.
10,344,365 B2 *    7/2019   Mueller ............... C22F 1/06
(Continued)

FOREIGN PATENT DOCUMENTS

JP       2009-221579 A    10/2009
JP         5333886 B2     11/2013
(Continued)

OTHER PUBLICATIONS

Office Action issued in corresponding Australian Patent Application No. 2015313647, dated Jul. 4, 2019.
(Continued)

*Primary Examiner* — Anthony J Zimmer
*Assistant Examiner* — Michael J Kachmarik
(74) *Attorney, Agent, or Firm* — McDermott Will & Emery LLP

(57) ABSTRACT

A device for fixing biological soft tissue is endowed with strength and deformation performance for being used as a device for coupling biological soft tissue that has been cut or separated due to an incision or the like during a surgical procedure, and is completely degraded in vivo and discharged after adhesion of the soft tissue or after healing of the incision tissue. The device is composed of a ternary Mg alloy material of Mg—Ca—Zn. In the Mg alloy material, the Ca and Zn are contained within the solid-solubility limit (Continued)

with respect to the Mg. The remainder is composed of Mg and unavoidable impurities. The Zn content is 0.5 at % or less. The Ca and Zn content has a relationship of Ca:Zn=1:x (where x is 1 to 3) by atom ratio. The crystal grain structure is equiaxed, the crystal grain size according to linear intercept being 30 to 250 μm.

13 Claims, 19 Drawing Sheets

(51) Int. Cl.
    *C22C 23/00*     (2006.01)
    *C22F 1/06*     (2006.01)
    *B21C 23/00*     (2006.01)
    *B22D 7/00*     (2006.01)
    *C22C 1/02*     (2006.01)
    *C22F 1/00*     (2006.01)

(52) U.S. Cl.
    CPC .............. *C22C 23/00* (2013.01); *C22C 23/04* (2013.01); *C22F 1/06* (2013.01); *C22F 1/00* (2013.01)

(56) References Cited

U.S. PATENT DOCUMENTS

| | | |
|---|---|---|
| 2015/0047756 A1 | 2/2015 | Washio et al. |
| 2016/0199186 A1* | 7/2016 | Tamai .................. B21C 23/001 623/23.53 |

FOREIGN PATENT DOCUMENTS

| | | |
|---|---|---|
| WO | 2013052791 A2 | 4/2013 |
| WO | 2013/069638 A1 | 5/2013 |
| WO | 2014001321 A1 | 1/2014 |

OTHER PUBLICATIONS

Written Opinion of the International Searching Authority dated Dec. 15, 2015 issued in International Patent Application No. PCT/JP2015/004596 (English translation).

* cited by examiner (1) 7 days after implantation  (2) 14 days after implantation (1) Immediately after implantation  (2) 28 days after implantation 28 days after implantation (1) No.1 Annealing material 350°C × 8 hours (2) No.1 Annealing material 400°C × 2 hours (3) No.1 Annealing material 450°C × 1 hour (1) Embodiment (2) Comparative Example 1

(3) Comparative Example 2

(1) 1 week 10
(a)

10
(b)

(2) 4 weeek 10 (a)

10 (b)

(1) 1week (2) 4week

DEVICE FOR FIXING BIOLOGICAL SOFT TISSUE, AND METHOD FOR PRODUCING SAME

CROSS-REFERENCE TO RELATED APPLICATIONS

This application is the U.S. National Phase under 35 U.S.C. § 371 of International Patent Application No. PCT/JP2015/004596, filed Sep. 9, 2015, which in turn claims the benefit and priority from Japanese Patent Application Number 2014-183716, filed Sep. 9, 2014 and Japanese Patent Application Number 2015-050101, filed Mar. 12, 2015, the subject matters of which are hereby incorporated by reference.

FIELD OF THE INVENTION

The present invention relates to a device for fixing biological soft tissue using a magnesium-based alloy material.

DESCRIPTION OF THE RELATED ART

Materials that are stable in vivo such as titanium materials have been used, for example, in surgical vascular clips, as prior-art devices for fixing biological soft tissue. Devices using titanium materials not only become unnecessary after suturing and healing the incision tissue, but cause problems such as metal artifacts (a phenomenon whereby artificial noise appears on the captured image when a highly dense, highly absorbent material such as a metal that has high X-ray absorption is present in the measurement target) during magnetic resonance imaging (MRI) and X-ray computed tomography (CT), interfere with prognostication, and the like because they remain semipermanently in the body.

On the other hand, magnesium, which is an essential biological element, is drawing attention as a structural material because high specific strength is obtained from a light weight. It also has excellent biocompatibility and is biodegradable, and is therefore expected to find application as a material for devices for fixing biological soft tissue. Pure magnesium, however, has low ductility, presenting a concern about rupturing of the device when biological soft tissue is fixed.

In recent studies as well, several magnesium-based alloy materials have been developed as materials for devices that are degraded in vivo. However, these materials are inadequate in terms of their deformability for use as a device for fixing biological soft tissue such as a surgical clip, staple, or the like.

For example, an Mg alloy material of Mg—Zn—RE having a long-period stacking structure with Zn and a rare earth element (RE: one or more of Gd, Tb, and Tm) contained in Mg is known as a conventionally known magnesium-based alloy material (see Patent Document 1). The problem, however, is that rare earth elements are expensive as a material and have inadequate deformability for use as a device for fixing biological soft tissue.

A ternary Mg alloy material of Mg—Ca—Zn that is inexpensive as it does not use rare earth elements and comprises elements that pose no problem of biotoxicity is also known as a conventionally known magnesium-based alloy material (see Patent Document 2). Nonetheless, there is concern about the rapid degradation rate in vivo because the amount of elements added is large. The magnesium-based alloy material disclosed in Patent Document 2 aims to increase the strength of magnesium, does not place importance on deformability, and a periodic structure which is a unique reinforced structure is not formed unless the average grain size is 1 μm or less.

Here, the characteristics of ternary Mg alloy materials of Mg—Ca—Zn having a crystal grain structure with an average grain size of 0.3-2 μm (Mg alloy materials serving as comparative examples) are described with reference to FIG. 24 and FIG. 25. FIG. 24 shows a characteristics graph of the compressive true stress-true strain relationship for materials subjected only to hot extrusion that conducts hot extrusion at 250° C. and not to annealing. The compressive true stress-true strain relationship corresponds to the compressive deformation. Four types of Mg alloy materials served as comparative examples, and the Ca and Zn content levels (atom %) of the Mg alloy materials are noted in the graphs of FIG. 24(1). The Mg alloy materials of Comparative Examples 1-4 could be confirmed to have low deformability because all of the alloys ruptured at a true strain of 0.15 or less. FIG. 24(2) shows an image observed by transmission electron microscope of the Mg alloy material of Comparative Example 4. The crystal grain size of the Mg alloy of Comparative Example 4 can be confirmed to be 1 μm or less based on FIG. 24(2).

FIG. 25 shows a characteristics graph of the compressive true stress-true strain relationship of a material subjected only to a hot extrusion process that conducts hot extrusion at 300° C. and not to annealing. The compressive true stress-true strain relationship corresponds to the compressive deformation. The Ca and Zn content levels (atom %) of the Mg alloy materials are the same as in the graph of FIG. 24(1). The Mg alloy materials of Comparative Examples 5-8 could be confirmed to have low deformability because all of the alloys ruptured at a true strain of 0.15 or less.

In addition, depending on the magnesium-based alloy material, magnesium is not the main component as the added concentration of alloy elements increases, and the problem is that the toxicity of ions or compounds generated by elution of added elements appears. In view of this, materials are known that ensure function as a magnesium-based biodegradable metal material that select only a low-biotoxicity element as one metallic element of a second component added to Mg, do not raise the concentration of the element added as the second component any more than necessary, and do not include precipitates and intermetallic compounds (see Patent Document 3). In the magnesium-based alloy materials of Patent Document 3, the toxicity of the elemental compound to the body depends on the concentration (amount) in the body, and the lower the amount of the element added, the lower the possibility of toxicity appearing. Therefore, the highest concentration of the content of the second component is set at about ⅓ of the solid-solubility limit concentration in magnesium for any remaining elements, except for elements with obvious biotoxicity.

Then, since the addition of Ca, Yb, Gd, In, and the like having a large metal bond radius lowers the steady-state degradation rate more than Au, Ag, Al, Zn, and the like having a small metal bond radius, the corrosion resistance of the alloy material is controlled by the type and amount of the second element added in magnesium-based alloy materials.

However, when the second component added to Mg is Zn or Ca, which are essential biological elements, the content thereof need not be set at about ⅓ of the solid-solubility limit concentration in magnesium. In addition, nothing is mentioned about ternary Mg alloy materials of Mg—Ca—Zn in Patent Document 3.

PRIOR ART DOCUMENTS

Patent Documents

Patent Document 1: Japanese Unexamined Patent Publication No. 2009-221579
Patent Document 2: International Publication Pamphlet WO 2013/069638
Patent Document 3: Japanese Patent No. 5333886

SUMMARY OF THE INVENTION

Problems to be Solved by the Invention

As described above, several magnesium-based alloy materials have been developed as materials for devices that are degraded in vivo. The problem, however, is that the deformability is inadequate for use as a device for fixing biological soft tissue such as a surgical clip, staple, or the like.

In view of this situation, an object of the present invention is to provide a device for fixing biological soft tissue, the device comprising a magnesium-based alloy material, wherein the device is endowed with strength and deformability for being used as a device for fastening biological soft tissue (organs, blood vessels, etc.) that has been cut or separated due to an incision or the like during a surgical procedure, and is completely degraded in vivo and excreted after suturing the soft tissue or healing the incision tissue.

Means for Solving the Abovementioned Problems

As a result of in-depth studies of addition contents (amounts) of zinc and calcium, which are essential biological elements, added to magnesium and methods for preparing magnesium-based alloys, the present inventors obtained findings indicating that a device comprising a ternary Mg alloy material of Mg—Ca—Zn of a specific composition is useful as a device for fixing biological soft tissue.

Specifically, the device for fixing biological soft tissue of the present invention is a device comprising a ternary Mg alloy material of Mg—Ca—Zn; the Mg alloy material contains Ca and Zn within the solid-solubility limit with respect to Mg, the remainder comprises Mg and unavoidable impurities, the Zn content is 0.5 atom % or less, the Ca and Zn content levels are such that Ca:Zn=1:x (where x is 1 to 3) by atomic ratio, and the crystal grain structure is equiaxed and has an average crystal grain size of 20-250 μm.

Such a configuration provides strength and deformability as a device for fixing biological soft tissue, as well as being completely degraded in vivo after suturing the soft tissue or after healing the incision tissue.

Here, when the Zn content becomes greater than 0.5 atom %, the in vivo degradation rate increases, and large amounts of gas are generated in association with degradation after implantation in the body. This is known to be a cause of delayed tissue recovery. The Zn content is therefore controlled to 0.5 atom % or less. In addition, when the Zn content becomes less than a Ca and Zn content of Ca:Zn=1:1 by atomic ratio, the problem is that the necessary ductility is not obtained. On the other hand, when the Zn content becomes greater than Ca:Zn=1:3, the problem is the rapid degradation rate exhibited.

The device for fixing biological soft tissue of the present invention comprises an equiaxed crystal grain structure having an average crystal grain size of 20-250 μm, and not only the strength but also the deformability can be improved by conducting annealing. Furthermore, the average crystal grain size is measured by the linear intercept method from an image of the crystal grain structure.

In addition, the device for fixing biological soft tissue of the present invention more preferably is a device comprising a ternary Mg alloy material of Mg—Ca—Zn; the Mg alloy material contains Ca and Zn within the solid-solubility limit with respect to Mg, the remainder consists of Mg and unavoidable impurities, the Zn content is from 0.2 atom % to 0.4 atom %, the Ca and Zn content levels are such that Ca:Zn=1:x (where x is 2 to 3), and the crystal grain structure is equiaxed and has an average crystal grain size of 20-250 μm.

The in vivo degradation rate is most preferably such that the tissue is joined and held for the period of 2-8 weeks it takes biological soft tissue to unite and, the device then degrades completely within about one year. To achieve this, the Zn content should be from 0.2 atom % to 0.4 atom %, and the relationship Ca:Zn=1:x (where x is 2 to 3).

The device for fixing biological soft tissue of the present invention comprises an equiaxed crystal grain structure having an average crystal grain size of 20-250 μm, and not only the strength but also the deformability can be improved by conducting annealing. The average crystal grain size may be measured by the linear intercept method from an image of the crystal grain structure.

Since high bending formability is required, the device for fixing biological soft tissue of the present invention should comprise a material in which crystal grain boundaries having crystal misorientation of 15° or more or crystal subgrain boundaries having crystal misorientation of from 3° to less than 15° have been formed, these being boundaries for dividing the crystal grain structure during deformation. A crystal grain boundary having crystal misorientation of 15° or more is an interface called a high-angle grain boundary, and the crystal grain structure is obviously divided during deformation. Alternatively, the crystal grain structure is divided during deformation even if the crystal misorientation is less than 15° as long as there is a crystal subgrain boundary. Furthermore, the reason the lower limit value of the crystal misorientation of the crystal subgrain boundary is set at 3° is because the lower limit value is defined as the limit value of crystal misorientation that can be confirmed by observation of the structure, and it was set at the minimum value (=3°) that can be observed by operating an electron beam in combination with a scanning electron microscope (SEM) and using the EBSD (electron back scatter diffraction) patterns that make it possible to measure the microcrystal orientation and crystal system.

Control should also be exerted by heat treatment so that an equiaxed crystal grain structure having an average crystal grain size of 20-250 μm after annealing is confirmed within the crystal grains of the Mg alloy material. This is related to preventing fracture due to stress concertation and makes it possible to raise the bending formability at normal temperature. Refining the crystal structure also has the advantage of increasing the strength after forming.

The device for fixing biological soft tissue of the present invention features a biodegradation residual ratio of 50-92% four weeks after implantation and an amount of gas generated in association with degradation of not more than twice the volume of the space formed during bioimplantation.

The device for fixing biological soft tissue of the present invention also features that the biodegradation rate can be controlled using the Ca and Zn content levels as parameters.

A method for producing the device for fixing biological soft tissue described above will be explained next.

The method for producing a device for fixing biological soft tissue is a method for producing a device comprising a ternary Mg alloy material of Mg—Ca—Zn that carries out the following steps 1)-7) in order.

1) A step for preparing an Mg alloy material by adding Ca and Zn to Mg within the solid-solubility limit so that the content of Zn relative to Mg is 0.5 atom % or less and the Ca and Zn content levels establish the relationship Ca:Zn=1:x (where x is 1 to 3) by atomic ratio 2) An ingot production step for producing an ingot by melting and casting the Mg alloy material 3) A homogenization heat treatment step for homogenization heat treatment of the ingot 4) A hot extrusion step for conducting hot extrusion at least once in a temperature range of 250-450° C.

5) An annealing step for conducting annealing in a temperature range of 350-450° C.

6) A forming step for forming into the desired device shape

7) A surface removal step for removing impurities including oxides on the device surface.

Here, the annealing step of 5) above may expose the ingot to high temperature for several tens of seconds immediately after extrusion by raising the hot extrusion temperature and slowing the hot extrusion rate in the hot extrusion step.

In the annealing step of 5) above, preferably, annealing is carried out for from one to eight hours at a temperature close to 400° C. when the Zn content relative to the Mg content is from 0.2 atom % to 0.4 atom % and the Ca and Zn content levels establish the relationship Ca:Zn=1:x (where x is 2 to 3) by atomic ratio in the Mg alloy material.

Carrying out hot extrusion in a temperature range of 250-450° C. makes it possible to form an equiaxed crystal grain structure having a grain size from the submicron order to about 10 μm.

In addition, conducting annealing in a temperature range of 350-450° C. makes it possible to form an equiaxed crystal grain structure having a crystal grain size of 20-250 μm after annealing.

Annealing is a heat treatment that removes internal distortion due to work hardening, grows the crystal grain structure, and improves deformability, and is conducted to obtain adequate strength and ductility for use as a clip. For example, the material is allowed to stand in air and cooled after heating to a temperature of 400° C. and holding for a certain length of time of about one to eight hours. The crystal grain size is measured by the linear intercept method from an image of the crystal grain structure; however, other known measurement methods may be used.

In addition, a first hot extrusion step for carrying out hot extrusion in a temperature range of 250-400° C. and a second hot extrusion step for carrying out hot extrusion at a temperature higher than the temperature in the first hot extrusion step and in a temperature range of 350-450° C. may be conducted instead of the hot extrusion step for carrying out hot extrusion in a temperature range of 250-450° C. and the annealing step for conducting annealing in a temperature range of 350-450° C. This is because the second hot extrusion step conducted at a higher temperature obtains the same effects as annealing.

Furthermore, a multi-stage hot extrusion step is also permissible rather than two steps comprising a first hot extrusion step and a second hot extrusion step. In this case, processing is conducted at a higher temperature in the hot extrusion step of the final stage than the temperature of the hot extrusion steps of previous stages.

The biodegradation rate can be controlled using the Ca and Zn content levels as parameters in the method for producing a device for fixing biological soft tissue of the present invention.

Effect of the Invention

The device for fixing biological soft tissue of the present invention is guaranteed to be safe even after degradation in the body because is it composed only of magnesium as the main component and calcium and zinc, which are essential biological elements, as added elements. It also has the strength and deformability to fix biological soft tissue, and also has the effect of making it possible to properly control the degradation rate.

DESCRIPTION OF THE PREFERRED EMBODIMENTS

Examples of embodiments of the present invention are explained in detail below with reference to the accompanying drawings. Furthermore, the scope of the present invention is not limited to the following examples and illustrated examples; numerous modifications and variations are possible.

Example 1

Figure 1:
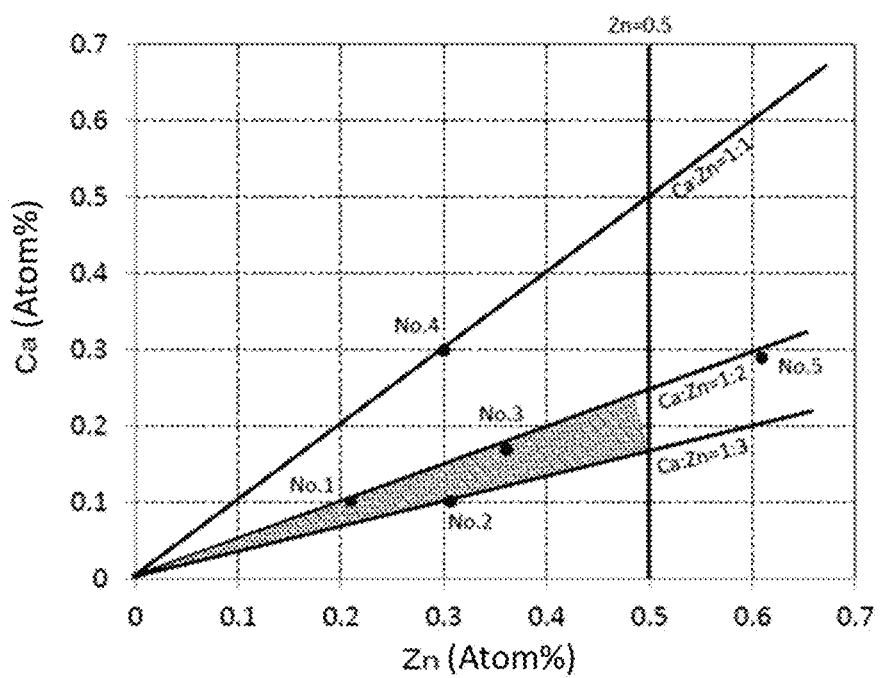
FIG. 1 shows a graph of the Ca and Zn content levels of ternary Mg alloy materials of Mg—Ca—Zn.

FIG. 1 is a graph of the Ca and Zn content levels of ternary Mg alloy materials of Mg—Ca—Zn. The results obtained by evaluating the utility of the five samples (Mg alloy materials No. 1-No. 5) shown in FIG. 1 as devices for fixing biological soft tissue are explained below. The five samples (Mg alloy materials No. 1-No. 5) were as shown in Table 1 below.

TABLE 1

| No. | Mg (atom %) | Ca (atom %) | Zn (atom %) | Fe (atom %) | Si (atom %) | Ni (atom %) | Ca:Zn (content ratio) | Comments |
|---|---|---|---|---|---|---|---|---|
| 1 | 99.69 | 0.10 | 0.21 | 0.002 | 0.003 | <0.001 | 1:2 (1:2.10) | Example A |
| 2 | 99.59 | 0.10 | 0.31 | 0.001 | <0.001 | <0.001 | 1:3 (1:3.10) | Example B |
| 3 | 99.48 | 0.16 | 0.36 | 0.001 | <0.001 | <0.001 | 1:2 (1:2.25) | Example C |
| 4 | 99.39 | 0.31 | 0.30 | 0.003 | 0.004 | <0.001 | 1:1 (1:0.97) | Example D |
| 5 | 99.10 | 0.29 | 0.61 | 0.002 | <0.001 | <0.001 | 1:2 (1:2.10) | Comparative Example |

Figure 2:
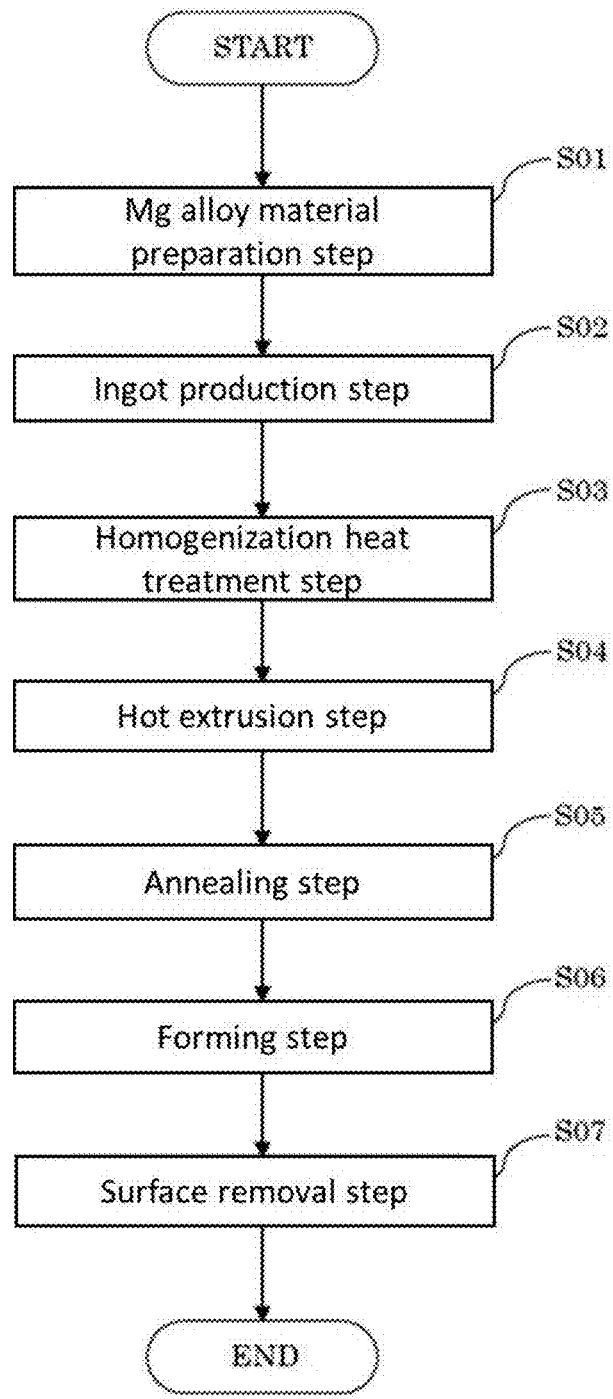
FIG. 2 is a production flow chart of a device for fixing biological soft tissue.

The production of the five samples (Mg alloy materials No. 1-No. 5) and the method for producing devices for fixing biological soft tissue using these Mg alloy materials will be explained with reference to FIG. 2.

First, an Mg alloy material is prepared by adding the Ca and Zn content levels relative to Mg in the amounts shown in Nos. 1-5 in Table 1 above by atomic ratio (S01: Mg alloy material preparation step). Then, the Mg alloy material is melted and cast to produce an ingot (S02: ingot production step).

Next, the ingot is subjected to homogenization heat treatment (S03: homogenization heat treatment step). Hot extrusion is then carried out in a temperature range of 300° C. (S04: hot extrusion step), and the crystal grain structure of the interior is refined by plastic working. Annealing is conducted thereafter in a temperature range of 400° C. (S05: annealing step). A homogeneous material can be obtained by holding for a long period of time after carrying out hot extrusion (S04).

The material is then formed into the desired clip shape (S06: forming step), and the impurities including oxides on the clip surface are removed (S07: surface removal step).

Finite element analysis of the strain distribution associated with fixation of the clip was conducted on clips made from the mesh models produced.

Figure 3:
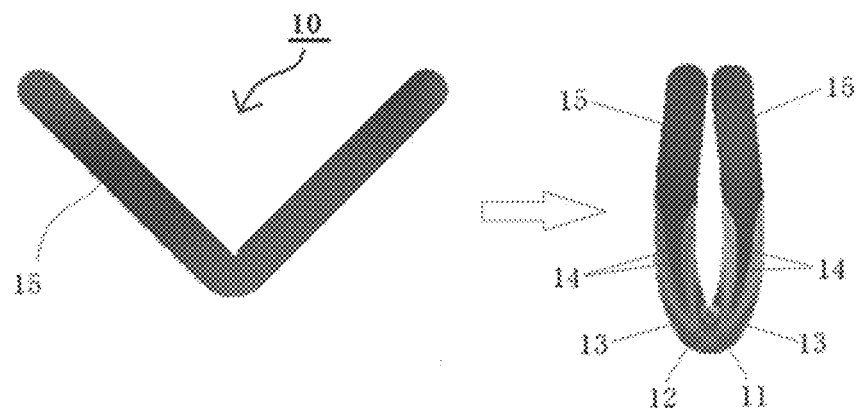
FIG. 3 is a strain distribution map of a produced clip.
Figure 26:
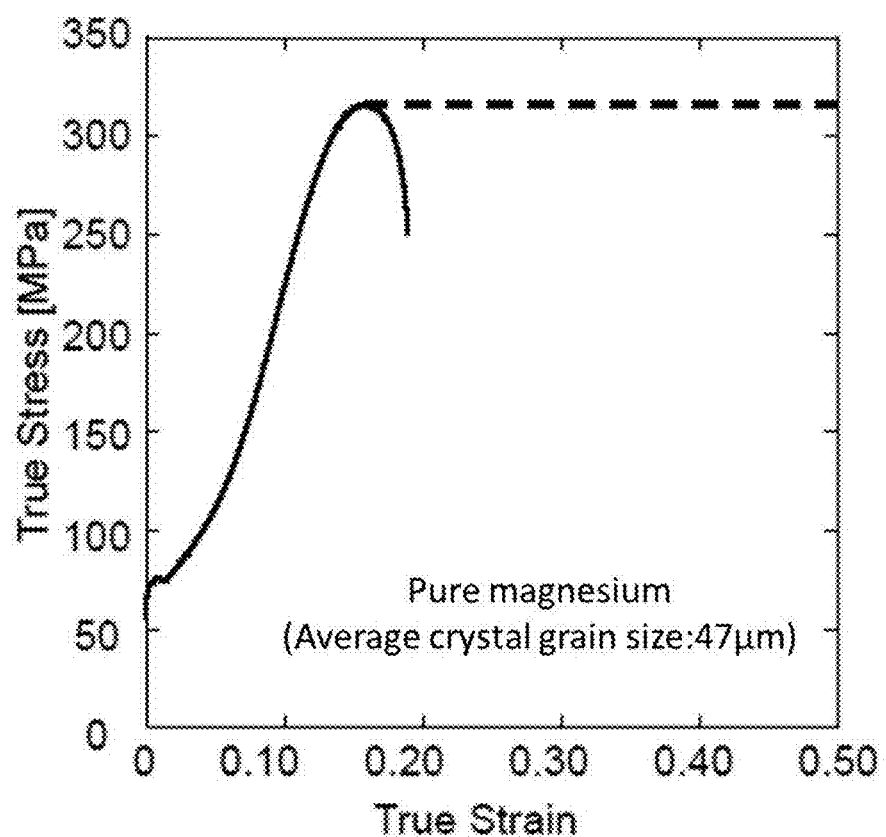
FIG. 26 shows a graph of the true stress-true strain relationship of pure magnesium used in finite element calculation of clips of the embodiment.

FIG. 3 is an equivalent plastic strain distribution diagram of a clip 10. The strain distribution diagram shown in FIG. 3 shows the results obtained by using finite element analysis based on the material data of pure magnesium (average crystal grain size: 47 μm). A graph of the true stress-true strain relationship of pure magnesium used in the finite element calculation of clip 10 is shown in FIG. 26. The dotted line in the graph of FIG. 26 is a plot assuming that the material reaches a constant value without rupturing even after stress has reached the maximum value. The left drawing in FIG. 3 shows a V-shaped clip (mesh model before deformation, open state before pinching); the right drawing shows the clip in a closed state. The locations labeled 11-15 in FIG. 3 each show a part with different shading on the image of the clip. The folded part 11 of the clip in a closed state is the part under the greatest strain, and the strain decreases in the order 12, 13, 14. The shaded part labeled 15 is a part under virtually no strain. Calculation showed the maximum relative plastic strain to be 0.357. This value of 0.357 changes depending on the clip material and shape, but is not changed by the size of the clip. Finite element analysis was conducted on the material parameters of pure magnesium and mesh model shapes of clips set and produced in the examples. When deformed into the shape in the right drawing of FIG. 3, the limit strain required for deformation was determined to be 0.357 using the maximum relative plastic strain value in the clip model. In other words, a value of 0.357 was set as one target indicator. Therefore, if the material used in the example is changed, the maximum strain value, that is, the limit value that serves as a target indicator, also changes since the strain distribution during deformation changes as well. Given that the clip shape and size are not limited, the maximum strain value of a clip of the mesh model shape used in the example serves as a benchmark in the present invention.

A material that does not break at a strain of 0.357 or more must be used in a clip of the mesh model shape used in the example. The tissue can be fixed without the clip rupturing at part 11 which is under the greatest strain in the clip produced. As will be described below, experimental results were obtained showing that the magnesium alloy produced in this example is a material that does not rupture at a true strain of 0.357 due to compression. It is thereby understood that biological soft tissue can be fixed using a clip made of a ternary Mg alloy material of Mg—Ca—Zn shown in the embodiment.

Figure 4:
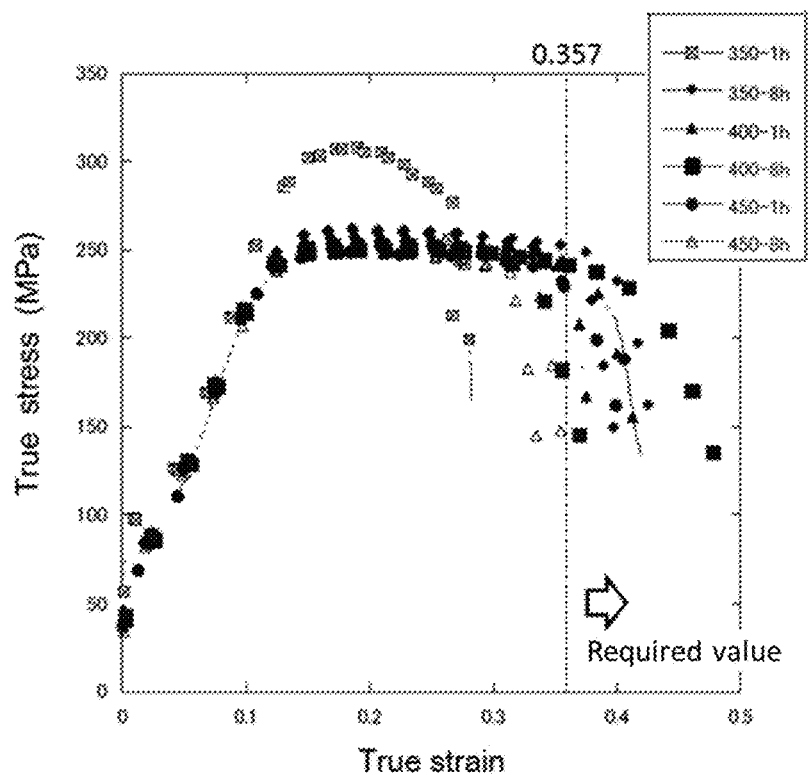
FIG. 4 shows a graph (1) of the true stress-true strain relations of annealed clips.

FIG. 4 relates to Mg alloy material No. 1 (Example A) and shows a graph of the true stress-true strain relations of clips annealed for one hour or eight hours at temperatures of 350° C., 400° C., and 450° C. In the graph of FIG. 4, the horizontal axis is the true strain, and the vertical axis is the true stress. It is understood from the graph of FIG. 4 that a clip made from Mg alloy material No. 1 (Example A) does not rupture even when strain of 0.357 or more arises, except under conditions of one hour at 350° C. and eight hours at 450° C. In other words, coarsening of the crystal grains is inadequate in heat treatment for one hour, and heat treatment for eight hours is necessary when the annealing temperature is low, such as 350° C. In addition, heat treatment for one hour is adequate and a crystal structure that clears strain of the required value of 0.357 or more can be obtained when the annealing temperature is high, such as 450° C. In contrast to this, the crystal structure coarsens more than is necessary in heat treatment for eight hours, and strain of the required value of 0.357 or more therefore cannot be cleared. This suggested the existence of an optimum annealing temperature range and holding time range.

Figure 5:
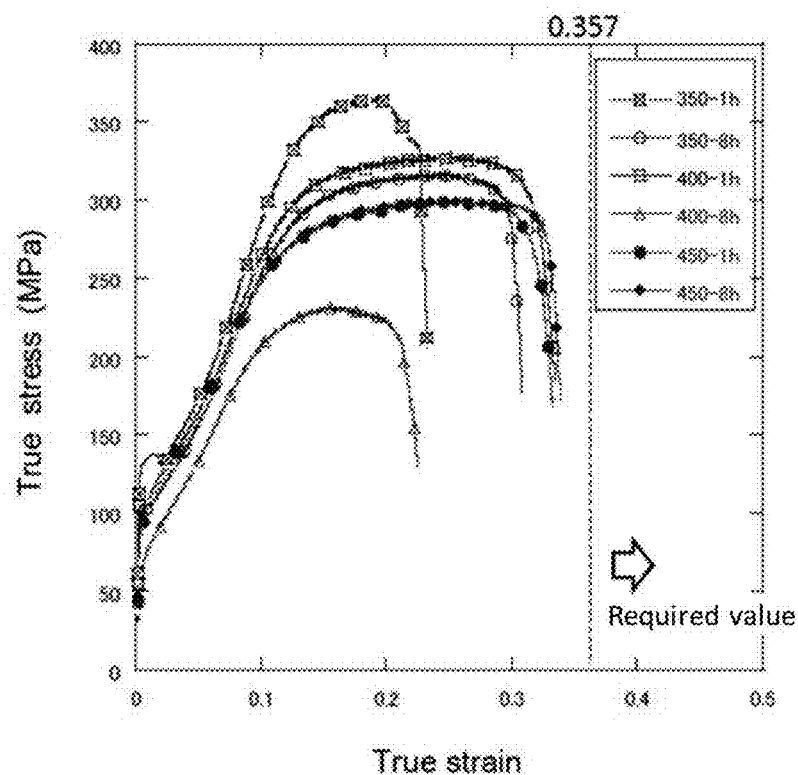
FIG. 5 shows a graph (2) of the true stress-true strain relations of annealed clips.

FIG. 5 relates to Mg alloy material No. 5 (Comparative Example) and shows a graph of the true stress-true strain relations of clips annealed for one hour or eight hours at temperatures of 350° C., 400° C., and 450° C. It is understood from the graph of FIG. 5 that a clip made from Mg alloy material No. 5 (Comparative Example) lacks reproducibility of data for clearing strain of the required value of 0.357 or more.

Figure 6:
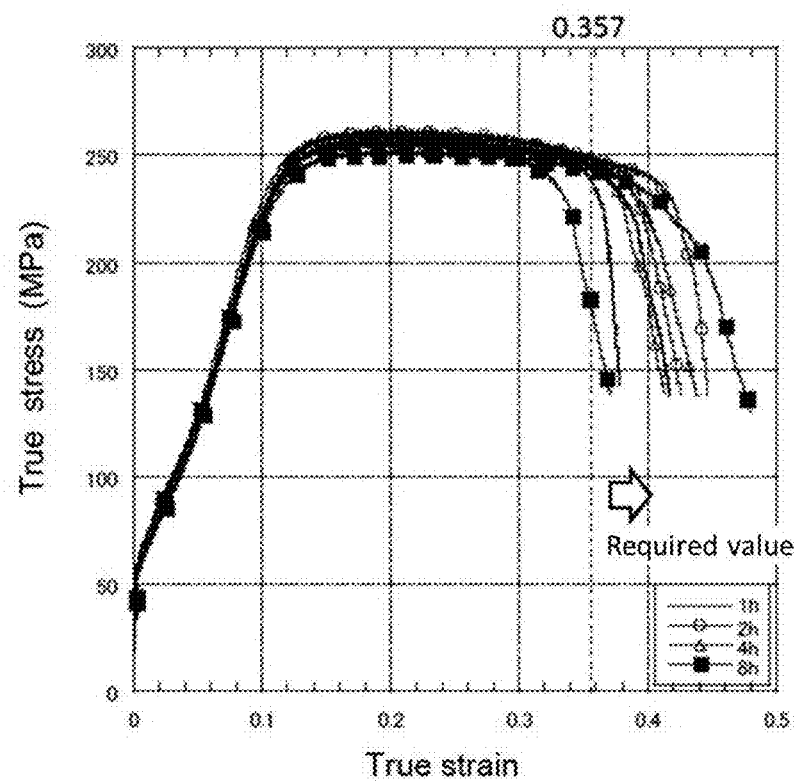
FIG. 6 shows a graph (3) of the true stress-true strain relations of annealed clips.

FIG. 6 shows a graph of the true stress-true strain relations of clips subjected to four types of annealing (one hour, two hours, four hours, or eight hours) at 400° C. in clips made from Mg alloy material No. 1 (Example A). Based on the graph of FIG. 6, the true stress-true strain relations sometimes improve and sometimes decline when annealing is conducted for eight hours in a clip made from Mg alloy material No. 1 (Example A). It is believed that the pinning effect of the solute atoms on the crystal grain boundaries declines and the crystal structure tends to coarsen partially when the annealing time is eight hours because the concentrations of the major solute atoms, which are calcium and zinc, are low in a material of Mg alloy material No. 1. This suggests that there is a possibility that the required value will not be satisfied when the annealing time is long when the solute atom concentration is low. This in turn suggested the existence of an optimum holding time range for annealing.

Figure 13:
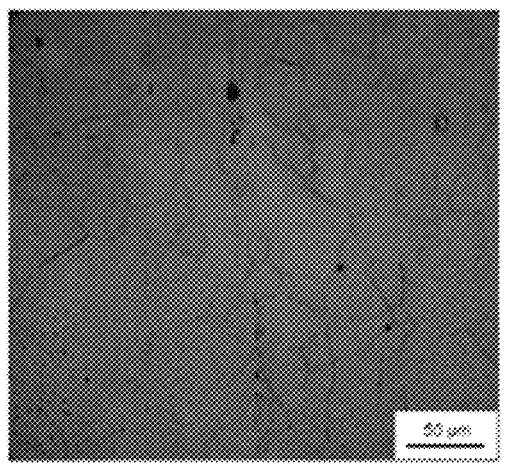
FIG. 13 shows a crystal grain structure micrograph.
Figure 13:
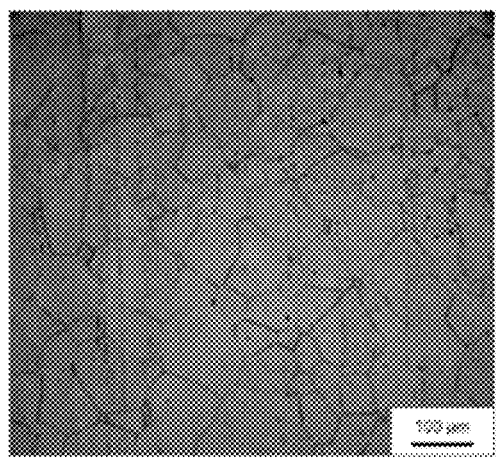
Figure 13:
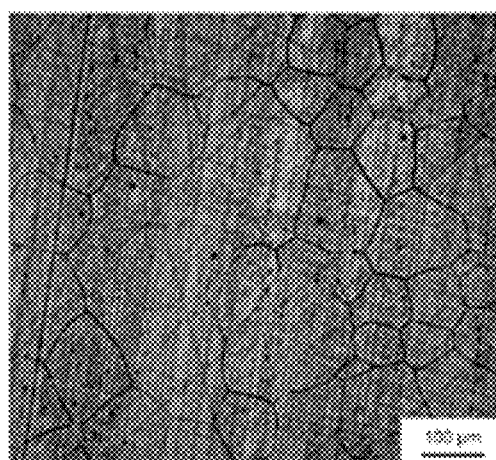

The crystal grain structure of a material that does not rupture even when strain of 0.357 or more arises will be explained here. FIGS. 13(1)-(3), respectively, relate to Mg alloy material No. 1 (Example A) and show crystal grain structure micrographs of clips annealed for eight hours at a temperature of 350° C., two hours at 400° C., and one hour at 450° C. Clips annealed for eight hours at 350° C., two hours at 400° C., and one hour at 450° C. do not rupture even when strain of 0.357 or more arises, as shown in FIG. 4 and FIG. 6 (see FIG. 4 for eight hours at 350° C., FIG. 6 for two hours at 400° C., and FIG. 4 for one hour at 450° C.). The crystal grain structure micrographs of FIGS. 13(1)-(3) make it possible to confirm that the crystal grain size of the annealed clips is about 20 µm for small grains and about 250 µm for large grains.

Figure 21:
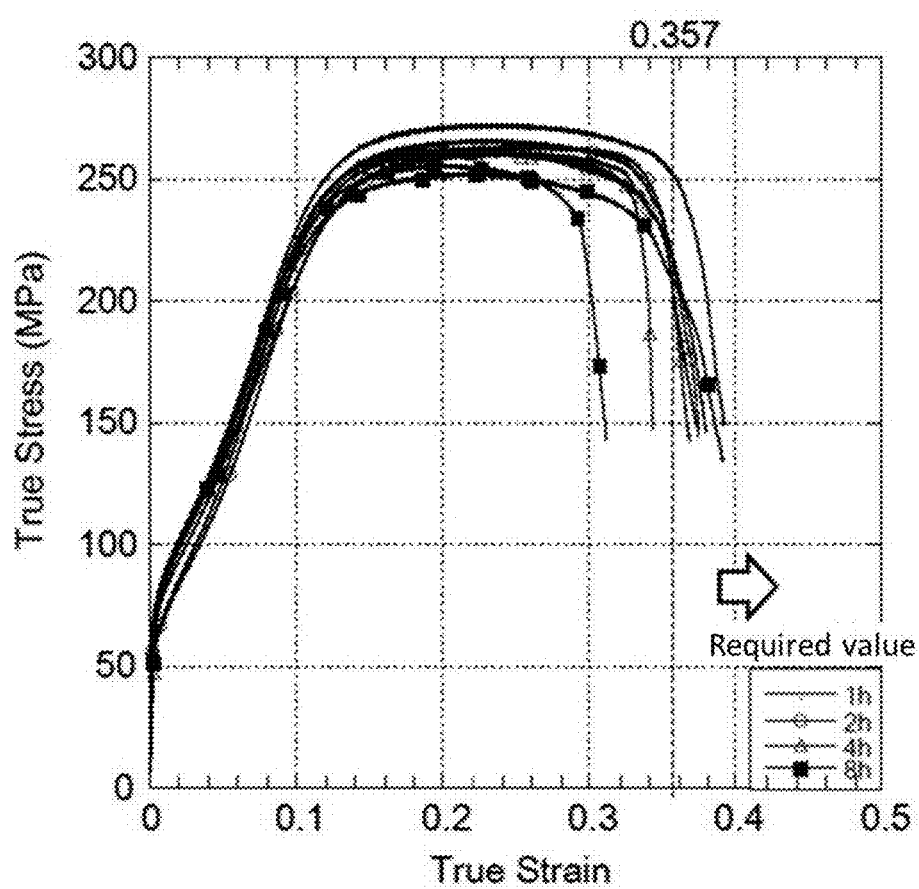
FIG. 21 shows a graph (4) of the true stress-true strain relations of annealed clips.

FIG. 21 shows a graph of the true stress-true strain relations of clips subjected to four types of annealing (one hour, two hours, four hours, or eight hours) at 400° C. in clips comprising Mg alloy material No. 2 (Example B). The graph of FIG. 21 confirmed that the true stress-true strain relations sometimes improve and sometimes decline when annealed for four hours or eight hours in clips made from Mg alloy material No. 2 (Example B), but that the true strain characteristics improve when annealed for one hour or two hours. This suggested the existence of an optimum holding time range in annealing in clips comprising Mg alloy material No. 2 (Example B).

Figure 22:
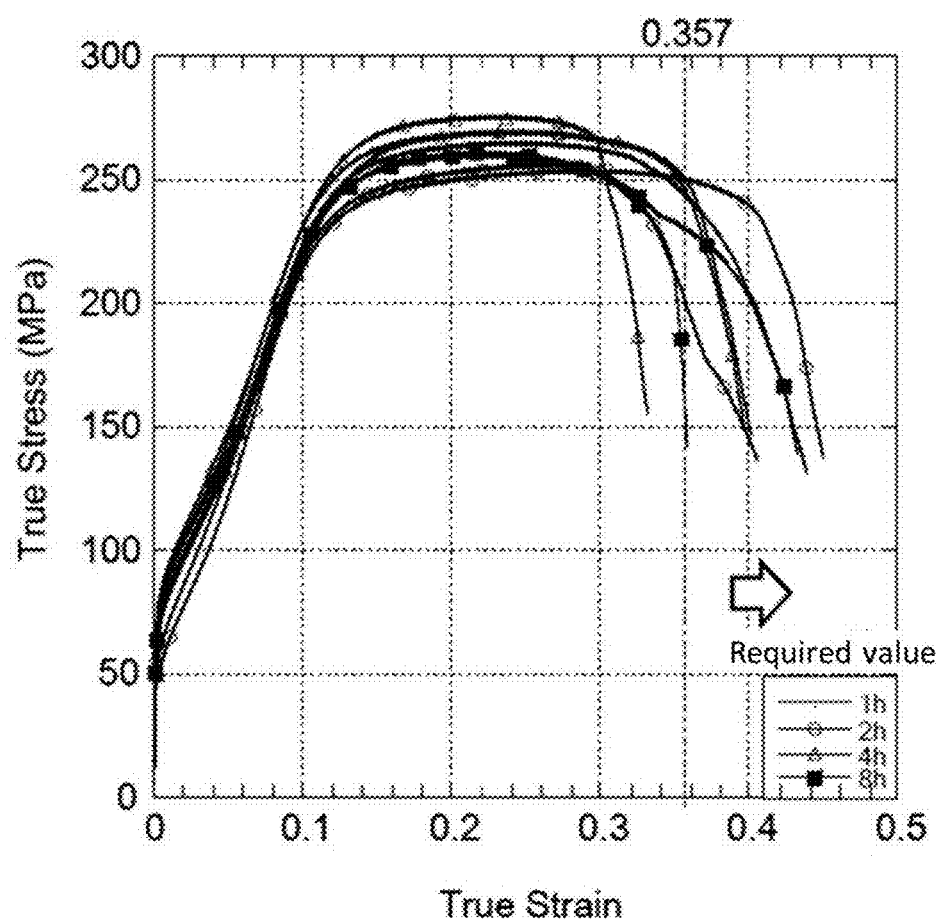
FIG. 22 shows a graph (5) of the true stress-true strain relations of annealed clips.

FIG. 22 shows a graph of the true stress-true strain relations of clips subjected to four types of annealing (one hour, two hours, four hours, or eight hours) at 400° C. in clips comprising Mg alloy material No. 3 (Example C). The graph of FIG. 22 confirmed that the true stress-true strain relations sometimes improve and sometimes decline when annealed for four hours and eight hours in clips comprising Mg alloy material No. 3 (Example C), but the true stress-true strain relations improve when annealed for one hour or two hours. This suggested the existence of an optimum holding time range for annealing in clips comprising Mg alloy material No. 3 (Example C).

Figure 23:
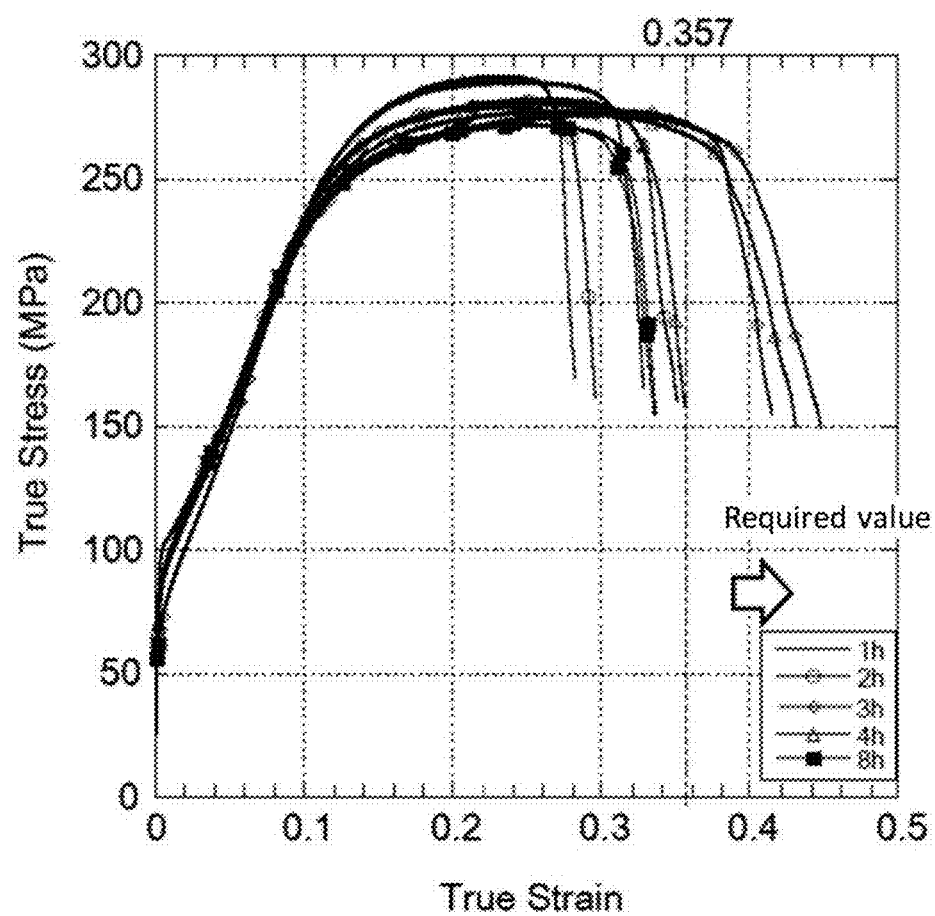
FIG. 23 shows a graph (6) of the true stress-true strain relations of annealed clips.
Figure 24:
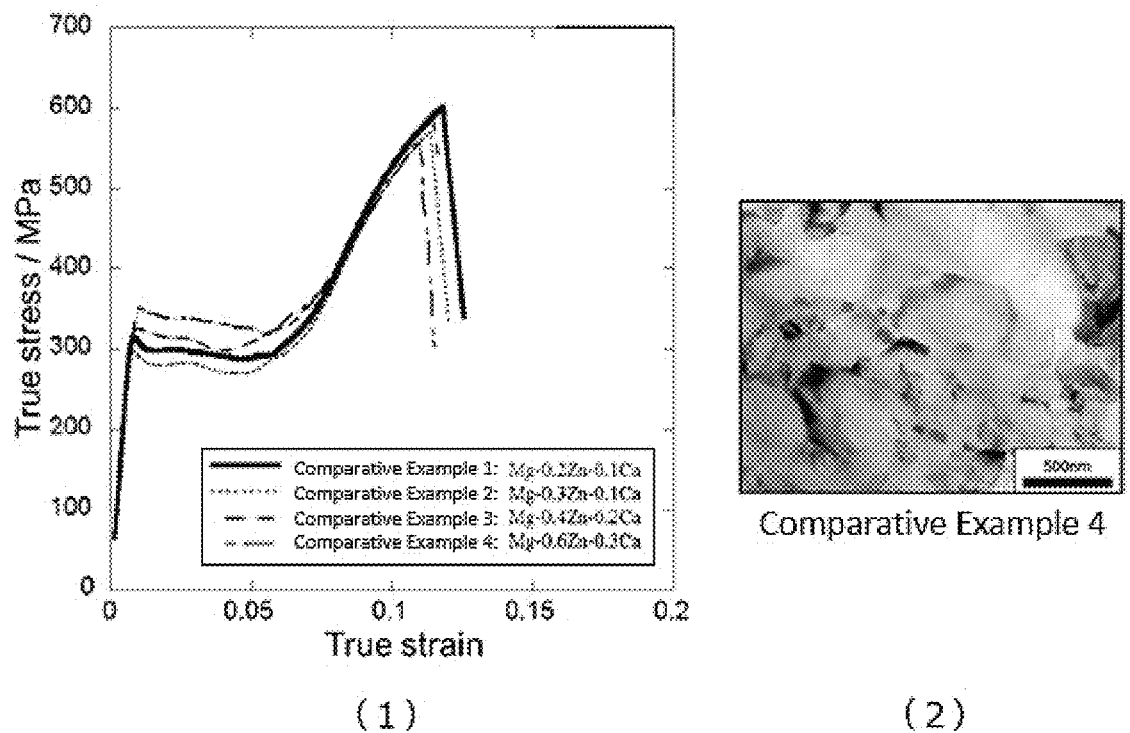
FIG. 24 is an explanatory drawing (1) of a conventional fine crystal grain material.
Figure 25:
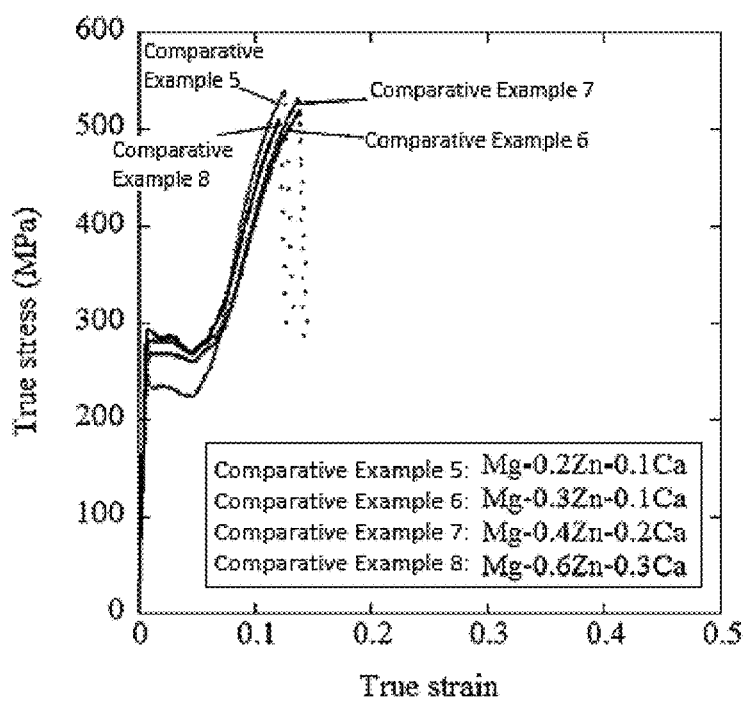
FIG. 25 is an explanatory drawing (2) of a conventional fine crystal grain material.

FIG. 23 shows a graph of the true stress-true strain relations of clips subjected to five types of annealing (one hour, two hours, three hours, four hour, or eight hours) at 400° C. in clips comprising Mg alloy material No. 4 (Example D). The graph of FIG. 23 confirmed that the true stress-true strain relations improve when annealed for three hours in clips comprising Mg alloy material No. 4 (Example D). In addition, the true stress-true strain relations were confirmed to sometimes improve and sometimes decline when annealed for four hours. However, those annealed for one hour, two hours, and eight hours were confirmed to lack reproducibility of data on clearing strain of the required value of 0.357 or more. This suggested the existence of an optimum holding time range for annealing in clips made of Mg alloy material No. 4 (Example D).

The results obtained by operating an electron beam in combination with a scanning electron microscope (SEM), conducting crystal orientation analysis using EBSD which can measure the crystal orientation and crystal system, and elucidating the plastic deformation behavior will be explained next.

Figure 7:
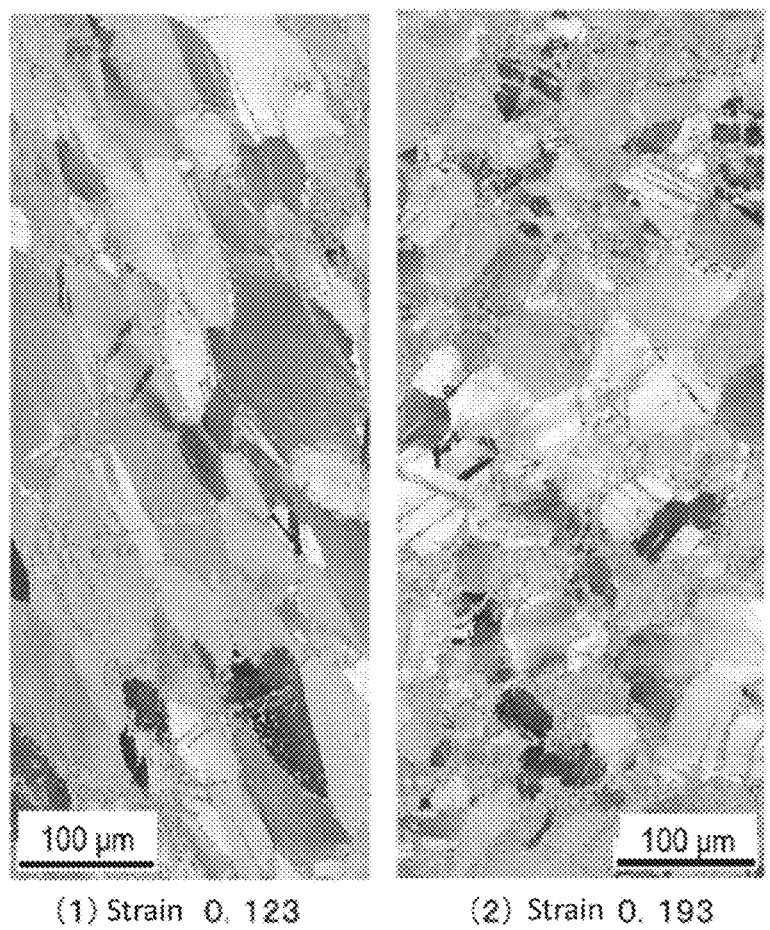
FIG. 7 shows the crystal orientation analysis results of annealed clips.

FIGS. 7(1) and (2) show the results of crystal orientation analysis of annealed cylindrical test pieces. FIG. 7(1) shows the crystal grain structure inside the recovered compressed test piece when the load was removed after compressing an Mg alloy material (No. 1: Example A) to a true strain of 0.123. FIG. 7(2) shows the crystal grain structure inside the recovered compressed test piece when the load was removed after compressing a cylindrical test piece made of an Mg alloy material (No. 1: Example A) to a true strain of 0.193. The "nominal stress ($\sigma_n$)-nominal strain ($\varepsilon_n$) relationship (curve)" was determined from the "load-displacement relationship (curve)" obtained by compression testing of the cylindrical test pieces under the respective conditions, and the strain value of the crystal grain structure was calculated by the "true stress ($\sigma_t = \sigma_n(1-\varepsilon_n)$)-true strain ($\varepsilon_t = -\ln(1-\varepsilon_n)$) relationship (curve)." Here, the nominal stress is the load divided by the initial cross-sectional area, and the nominal strain is the (initial height of the test piece-height after deformation) divided by the initial height of the test piece.

Boundaries having misorientation of several degrees are confirmed every several microns inside the crystal grains of the Mg alloy material in the compressed specimen corresponding to the closed state of the clip shown in FIG. 7(2), that is, during deformation. It is thereby understood that the strain accumulated in association with deformation is dynamically recovered due to the formation of subgrains, the formation of cracks (microscopic cracks) due to stress concentration is avoided by the occurrence of "dynamic recovery," and this contributes to improving the ductility.

Figure 8:
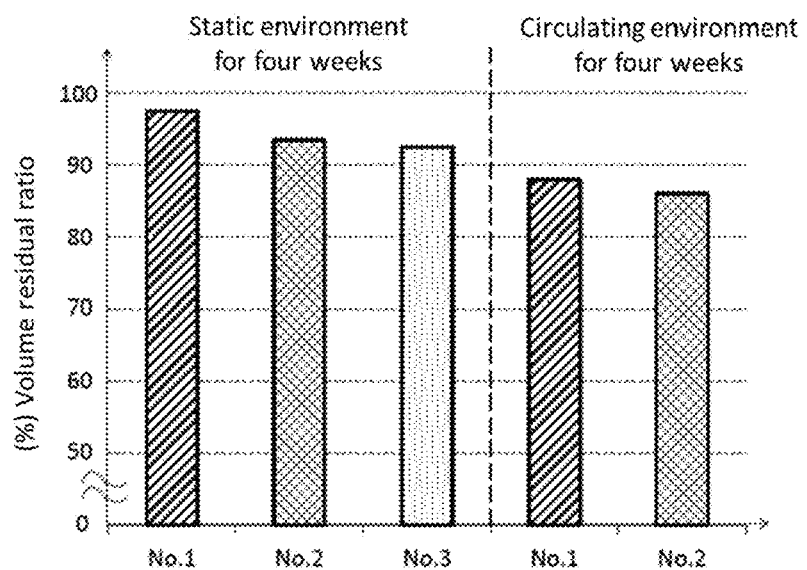
FIG. 8 shows a graph of the biodegradability of annealed clips.

FIG. 8 shows a graph of the biodegradability of annealed clips. These are the results of in vitro tests conducted by immersion for a certain period of time in a solution simulating body fluid (E-MEM: 10% FBS, $CO_2$ concentration: 5%, 37° C.)

The left side of the graph of FIG. 8 relates to Mg alloy materials Nos. 1-No. 3 and shows the volume residual ratio of the clip when an environment similar to that within the body was constructed, and the clip produced was left in the static environment for four weeks. The right side of the graph relates to Mg alloy materials No. 1 and No. 2 and shows the volume residual ratio of the clip when an fluid circulating environment similar to that within the body was constructed, and the clip produced was allowed to stand for four weeks in the slowly refluxed solution described above, that is, allowed to stand for four weeks in a circulating environment. Here, the volume residual ratio is taken to be the ratio determined as a result of dividing the residual volume of the magnesium alloy calculated from CT observation images by the volume before immersion.

It is understood from the graph of FIG. 8 that the volume residual ratios of clips after four weeks in a static environment are all 90% or greater, the residual ratios of the clips after four weeks in a circulating environment are all 85% or greater, and the biodegradation rates are appropriate as a device for fixing biological soft tissue. In addition, since the volume residual ratio increased in the order Mg alloy material No. 1 (Example A), No. 2 (Example B), No. 3 (Example C) according to the in vitro test method immersed for a certain period of time in a solution simulating body fluid described above, the biodegradation rate is understood to lengthen in this order. It is also understood from this that the biodegradation rate can be adjusted by the Ca and Zn concentrations.

As described above, devices using Mg alloy materials No. 1-No. 3 were clarified to be useful as devices for fixing biological soft tissue.

Example 2

The biodegradability and safety of the device for fixing biological soft tissue produced were confirmed in Example 2. An explanation follows.

Figure 9:
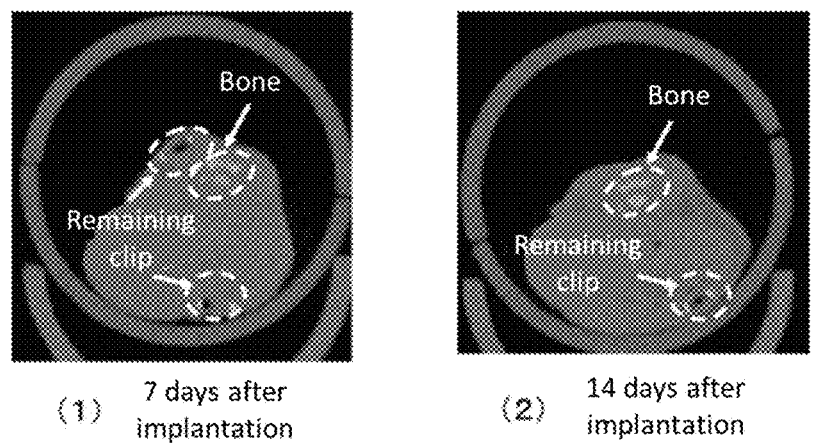
FIG. 9 shows an X-ray CT sectional image (1) after implanting an annealed clip in vivo.
Figure 10:
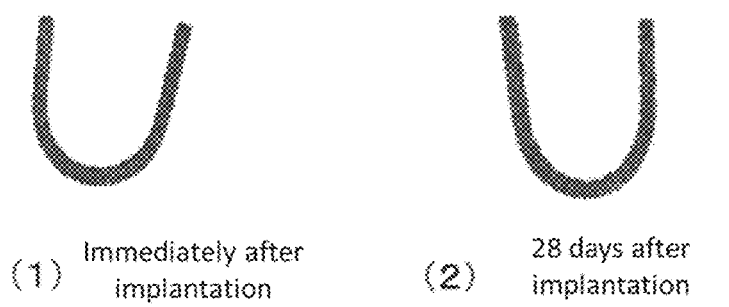
FIG. 10 shows an X-ray CT sectional image (2) after implanting an annealed clip in vivo.

FIG. 9 and FIG. 10 show X-ray CT sectional images of a U-shaped device for fixing biological soft tissue produced by the same method as in Example 1, that is, by annealing, after implantation in the body of a mouse.

The device for fixing biological tissue was confirmed based on the X-ray CT sectional images to maintain its U-shape 7, 14, and 28 days after implantation.

FIG. 9(1) is an image of seven days after implantation in a mouse. FIG. 9(2) is an image of 14 days after implantation in a mouse. In both cases, the changes in the volume of the space from immediately after implantation are very slight. The amount of gas generated is therefore understood to be minute, and no rapid gas generation is found.

FIG. 10(1) is a reconstructed image of an X-ray CT sectional image of immediately after implantation in a mouse. FIG. 10(2) is a reconstructed image of an X-ray CT sectional image of 28 days after implantation in a mouse. Although a decrease in volume due to uniform degradation is found after 28 days, the reconstructed device is understood to maintain its U-shape. It is thereby understood that the device maintains its fastening performance during this period without any parts missing. Furthermore, it was confirmed that no lesions were seen based on X-ray CT or visual observation of the surrounding tissues at the time of extraction.

The biodegradability of a device made of titanium (Comparative Example 1) and a device having a high Zn content (Comparative Example 2) will be described here as comparative examples.

Figure 11:
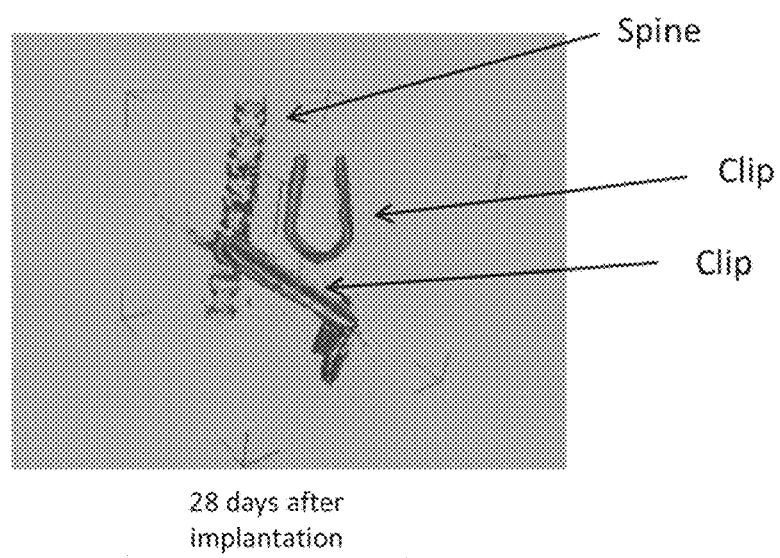
FIG. 11 shows an X-ray CT sectional image after implanting a titanium device (Comparative Example 1) in vivo.
Figure 12:
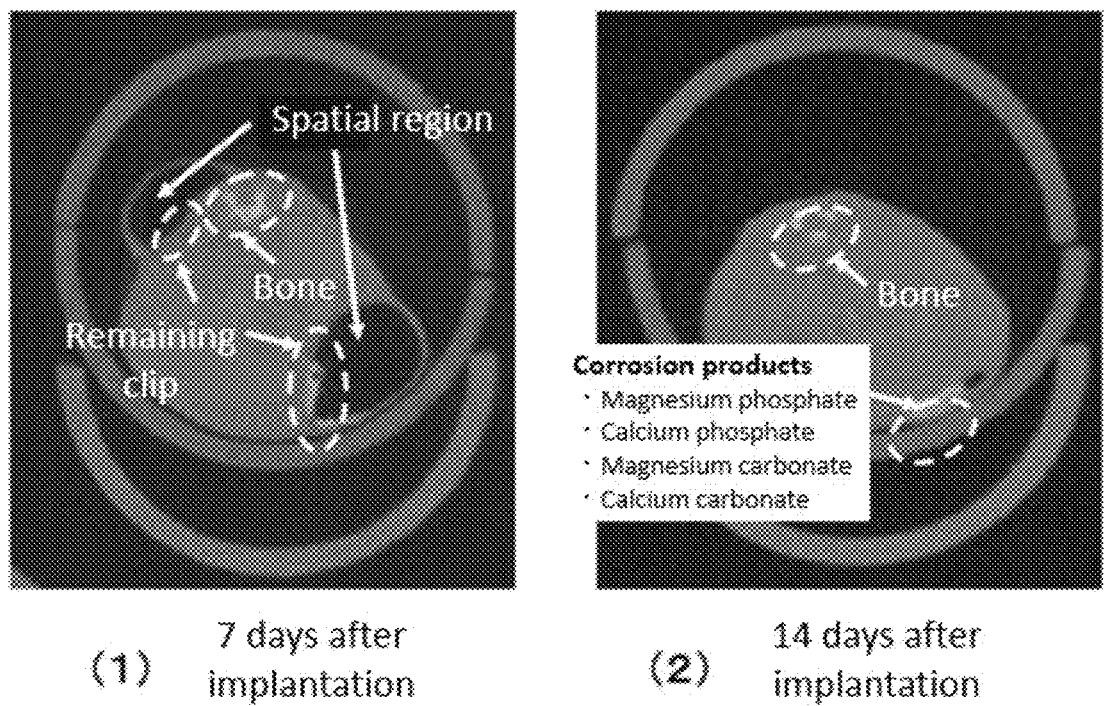
FIG. 12 shows an X-ray CT sectional image after implanting a device having a high Zn content (Comparative Example 2) in vivo.

FIG. 11 shows an X-ray CT sectional image of after implantation of a titanium device (Comparative Example 1) in vivo. FIG. 12 shows an X-ray CT sectional image after implantation of a device having a Zn content of 6 atom % (Comparative Example 2) in vivo.

The titanium device (Comparative Example 1) is understood to maintain its shape without degrading even 28 days after implantation in a mouse (see FIG. 11). Although not shown in the drawing, the titanium device (Comparative Example 1) has a large artifact effect on the X-ray CT sectional image and can be said to make observation of the biological tissue difficult.

On the other hand, the Mg alloy material including a large amount (6 atom %) of zinc generated a large amount of gas (hydrogen) in association with biodegradation after seven days due to its rapid biodegradation rate. FIG. 12(1) shows an X-ray CT sectional image of seven days after implantation in a mouse. In FIG. 12(1), there is a black spatial region showing a trace of a gas pool remaining after the device has disappeared, and there is a clear part on the edges of the spatial region; it was possible to confirm a metal structure, which is the remaining clip, and bone.

In addition, the metal structure degraded completely after 14 days, changing into compounds such as calcium phosphate, magnesium phosphate, magnesium carbonate, and calcium carbonate, and corrosion products of the device remained in the body of the mouse. FIG. 12(2) shows an X-ray CT sectional image of 14 days after implantation in a mouse. Corrosion products are difficult to discern when buried in soft tissue because their contrast is lower than that of bone, but parts of corrosion products (calcium phosphate, magnesium phosphate, magnesium carbonate, calcium carbonate) can be confirmed in FIG. 12(2).

In comparison to the changes over time in the materials of the above two Comparative Examples 1 and 2, the device for fixing biological soft tissue of the present invention is understood to have performance that makes it possible to avoid delayed tissue recovery associated with the generation of a large amount of gas, to have fastening and holding performance for a suitable length of time within the body, and to be minimally harmful to the body.

Example 3

<Subcutaneous Implantation Test in the Abdomen of Mice>

The results of a study that implanted clips produced by the same method as in Example 2 (referred to hereinafter as clips of the present example) subcutaneously to the abdomen of mice will be explained first. Titanium clips (Comparative Example 1) and clips having a Zn content of 6 atom % (Comparative Example 2) were also tested by subcutaneous implantation to the abdomen of mice in the same way as comparative examples.

Although no growth of the space due to gas generation could be observed upon external observation with the clips of the embodiment or the titanium clip (Comparative Example 1) one week after implantation, growth of a large space was seen with the clip of Comparative Example 2 having a high Zn content. The clip of Comparative Example 2 having a high Zn content appeared to have generated a large amount of gas (hydrogen) in association with biodegradation after one week due to its rapid biodegradation rate.

Figure 14:
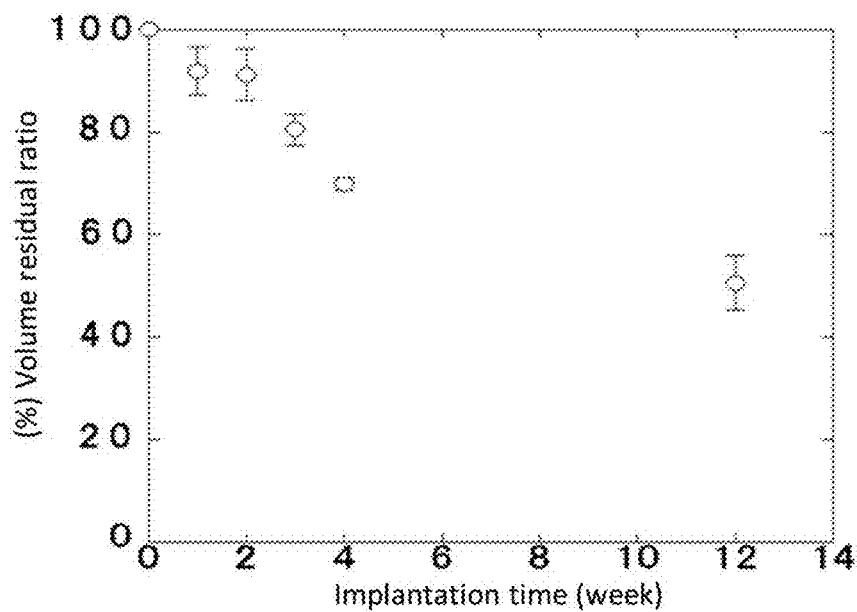
FIG. 14 shows a graph of the implantation time and the volume residual ratio (Example 3)
Figure 15:
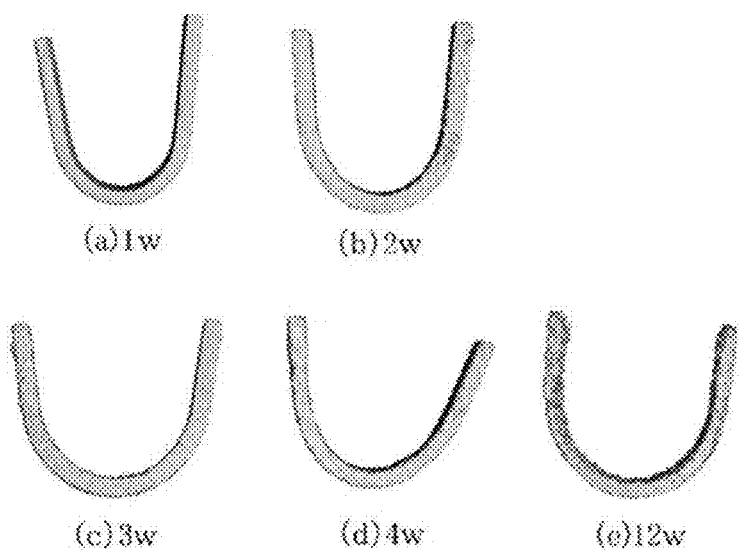
FIG. 15 shows reconstructed images of X-ray CT sectional images (Example 3)

FIG. 14 shows a graph of the implantation time and the volume residual ratio of clips of the embodiment. The graph plots the mean values of three mice used in the test. As shown in FIG. 14, the clips of the embodiment decreased in volume over time in the body of the mouse, and reached 70% one month (four weeks) after implantation and 50% three months (12 weeks) after implantation.

FIGS. 15(a)-(e), respectively, show reconstructed images of X-ray CT sectional images of clips of the embodiment one week, two weeks, three weeks, four weeks, and 12 weeks after implantation in mice. FIG. 15 confirmed that clips of the embodiment retain the shape of the clip at the time of implantation after 12 weeks.

Next shown are the results obtained by measuring the Mg ion concentration and the like in the body 12 weeks after implantation. The measurement targets are shown below in Table 2. The serum test data were also analyzed statistically. Furthermore, in statistical analysis, the data were assumed to have a normal distribution, the variance was judged by F-test, and those of equal variance were subsequently analyzed using Student's t-test and those of unequal variance were analyzed by Welch's t-test. The significance level was set at $p<0.05$ in all analyses.

TABLE 2

| Measurement target | Explanation |
| --- | --- |
| Mg (mg/dL) | Blood magnesium level |
| CRE (mg/dL) | Creatinine (numerical value rises as renal function declines) |
| AST (IU/L) | Aspartate aminotransferase (numerical value rises in association with disorders of the liver and myocardium) |
| ALT (IU/L) | Alanine aminotransferase (numerical value rises due to destruction of cells in the liver) |
| ALP (IU/L) | Alkaline phosphatase (numerical value rises due to abnormalities of the hepatobiliary system, obstruction and stenosis of the biliary tract) |

Figure 16:
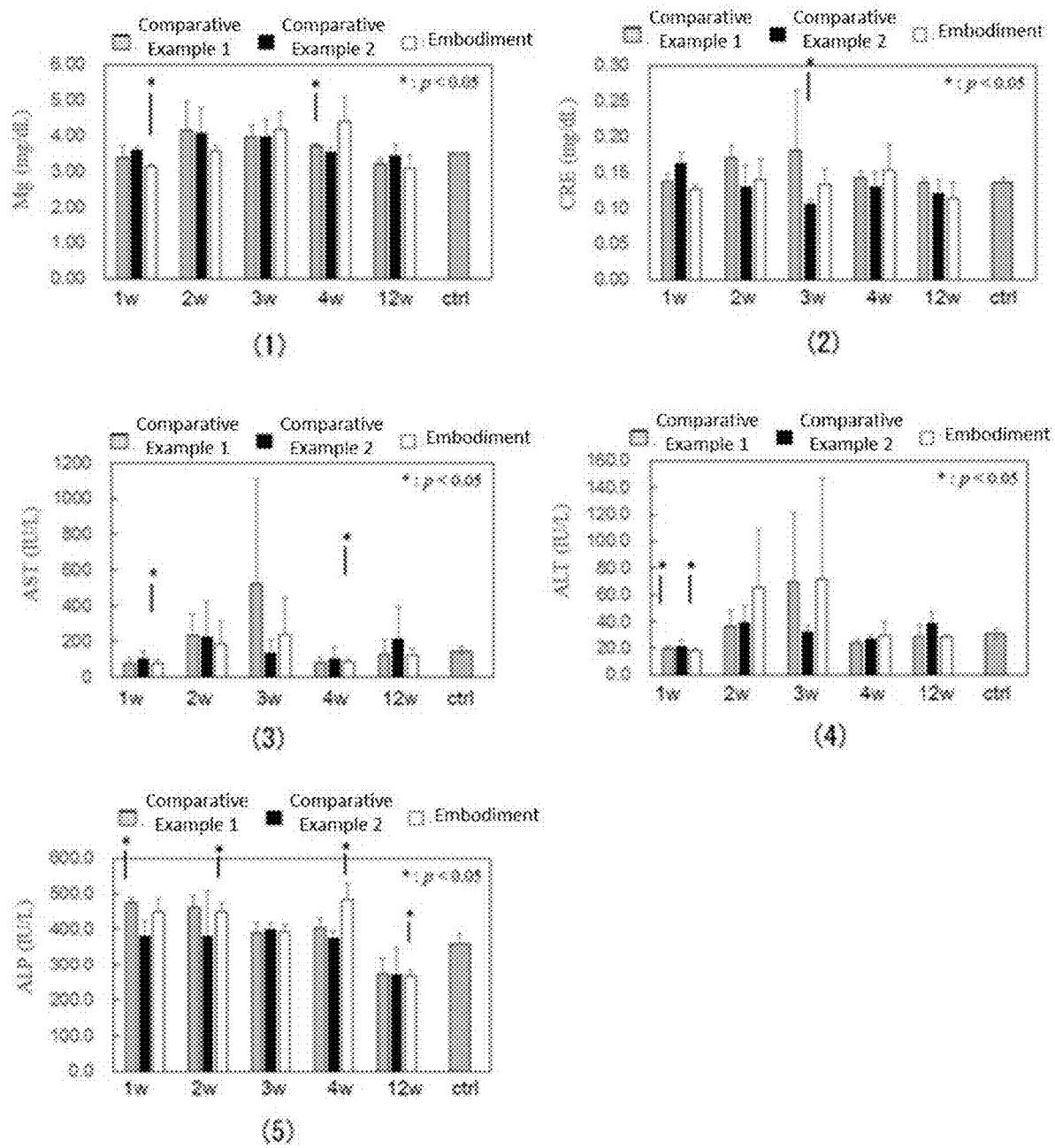
FIG. 16 shows graphs of the measurement of the Mg ion concentration, etc. in the blood (Example 3)

FIG. 16 shows graphs of the measurement results of the blood Mg ion concentration and the like in the body up to 12 weeks after implantation. Each of the graphs of FIGS. 16(1)-(5) shows the numerical values of Mg, CRE, AST, ALP, and ALT after one week, two weeks, three weeks, four weeks, and 12 weeks for the clips produced (embodiment), titanium clips (Comparative Example 1), and clips having high Zn (Comparative Example 2), respectively. In the bar graphs, data from after elapse of the predetermined length of time are arranged in three bars from left to right in the order Comparative Example 1, Comparative Example 2, embodiment. The far right bar of each graph shows the numerical values after four weeks taking normal mice not subjected to laparoscopy or implantation as a control. Furthermore, the data in the graphs are the mean of the data from three mice.

The fact that the results obtained by measuring the blood Mg concentration up to 12 weeks after implantation did not reveal a significant increase in concentration makes it possible to confirm that the eluted ion is excreted outside the body.

Figure 17:
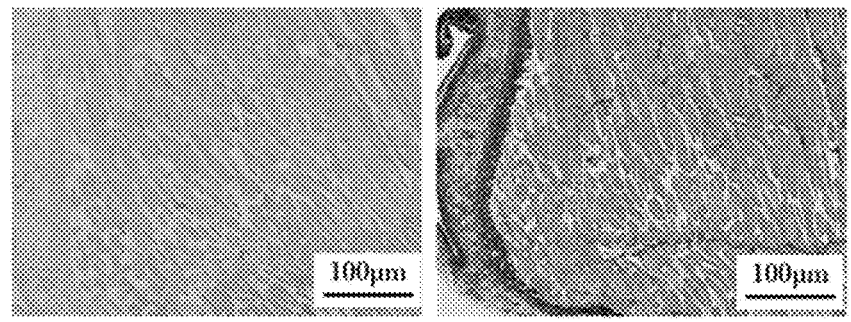
FIG. 17 shows the results of observation of the surrounding cells and tissues (Example 3)
Figure 17:
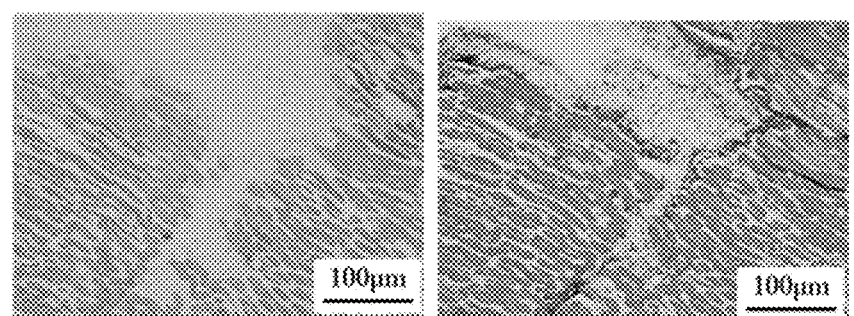
Figure 17:
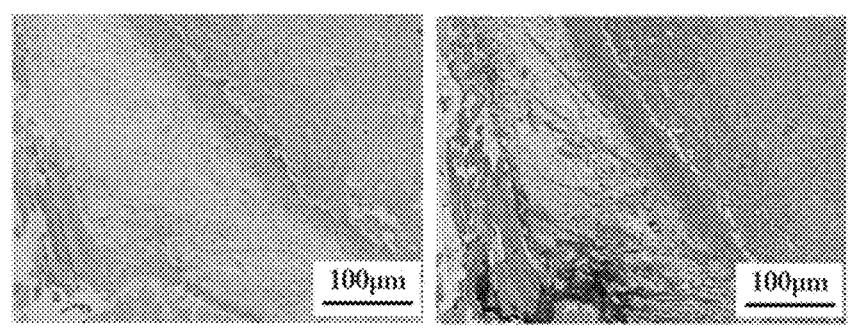

FIG. 17 shows the results of observation of the surrounding cells and tissues two weeks after implantation. FIGS. 17(1)-(3) show the results obtained by staining the cells and tissues surrounding the implanted clip produced (embodiment), titanium clip (Comparative Example 1), and clip having a high Zn content (Comparative Example 2) by hematoxylin-eosin stain (HE stain) and SR stain by Sirius red (images on the left are HE stain; images on the right are SR stain).

There was no inflammatory response, the surrounding cells and tissues were normal, and the clip of the embodiment was confirmed to be biologically safe based on cell observation of the cells and tissues surrounding the implanted clip produced (embodiment) and the cells and tissues surrounding the implanted titanium clip (Comparative Example 1). On the other hand, fibrous morphology was not seen, intercellular substrate (cell walls) was destroyed, nuclei were not formed in cells, and the tissue appeared necrotic in observation of the cells and tissues surrounding the implanted clip having high Zn (Comparative Example 2).

Example 4

<Vascular Anastomosis Test Using Rats>

Example 4 confirmed the biodegradability and safety of clips produced, unlike the clip production methods of Examples 2 and 3, by raising the hot extrusion temperature and slowing the hot extrusion rate in the hot extrusion step to expose the ingot to a high-temperature state for several tens of seconds immediately after extrusion and conducting annealing immediately after the hot extrusion step. An explanation follows.

The clips of Example 4 have the Zn and Ca contents of the Mg alloy material of No. 1 in Table 1 described above in Example 1. Specifically, 0.1 atom % of Ca and 0.21 atom % of Zn were added relative to 99.69 atom % of Mg, an ingot was produced by melting and casting, and the ingot was subjected to homogenization heat treatment. After heat treatment, the ingot was subjected to stage one hot extrusion at 350° C., and the ingot 90 mm in diameter was processed to a diameter of 22 mm. The diameter was brought to 20 mm by cutting the 22 mm diameter, the ingot was subjected to stage two hot extrusion at 410° C., and processed into a V-shaped cross-section. Annealing by exposure to 400-410° C. was conducted immediately after the stage two hot extrusion. Impurities including oxides were subsequently removed from the clip surface.

Figure 18:
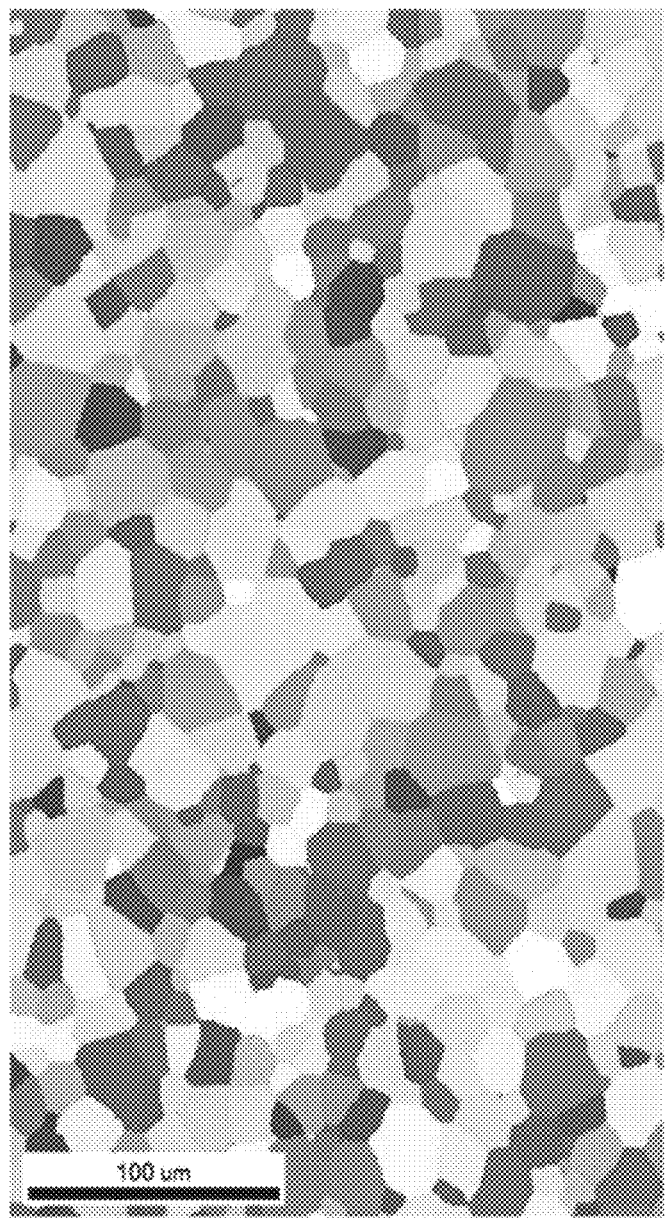
FIG. 18 shows the crystal orientation analysis results by EBSD (Example 4)

FIG. 18 shows the results obtained by operating an electron beam in combination with a scanning electron microscope (SEM) and conducting crystal orientation analysis of the clips produced using EBSD, which can measure the microcrystal orientation and crystal system. The crystal orientation analysis results shown in FIG. 18 confirmed the crystal structure of the clips produced to be an equiaxed crystal grain structure. In addition, the average crystal grain size of the crystal structure of the clips produced measured using the intercept method was 28.8 (μm) near the valley of the V-shape of the clip and 31.5 (μm) near the top of the V-shape.

The clips produced were confirmed to have an equiaxed crystal grain structure having an average crystal grain size of approximately 30 (μm). These clips have excellent deformability in a closed V-shape because, as explained in FIG. 7, boundaries having misorientation of several degrees appear every several microns within the crystal grains (subgrains are formed), the strain accumulated in association with deformed state is dynamically recovered, and the formation of cracks due to stress concentration is avoided (relaxation of stress concentration).

Next, the results obtained by anastomosing a blood vessel connected to part of the rat liver and the bile duct using the clips produced will be explained. The abdomen of the rat was cut open, a blood vessel connected to part of the liver and the bile duct were placed together and anastomosed by closing the V-shaped clip. The liver was subsequently resected.

Figure 19:
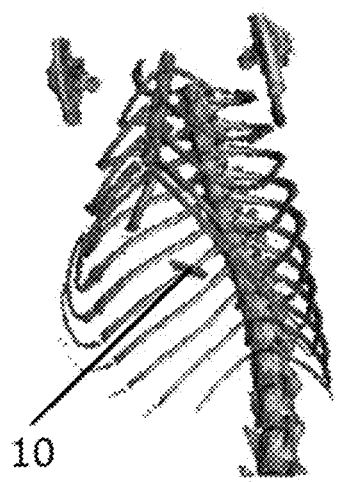
FIG. 19 is reconstructed images 1 of X-ray CT sectional images of a rat (Example 4)
Figure 19:
Figure 19:
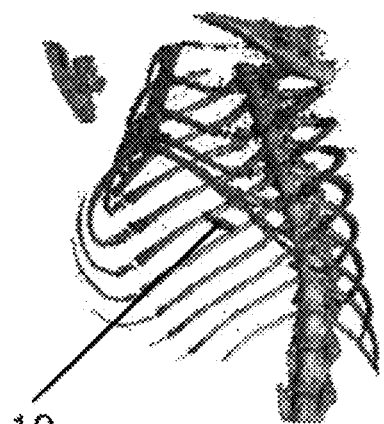
Figure 19:
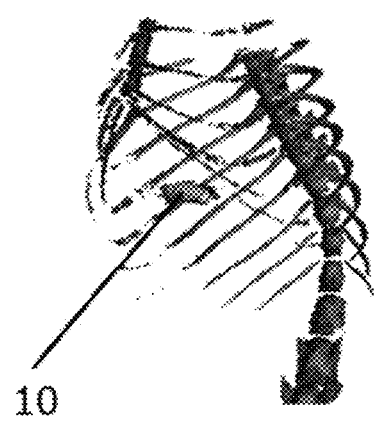

FIG. 19 shows reconstructed images of X-ray CT sectional images of the chest of the rat one week and four weeks (one month) after resection. In FIG. 19, (1) shows the reconstructed images one week after resection and (2) shows those four weeks (one month) after resection. In FIGS. 19(1) and (2), (a) was anastomosed by a clip of the embodiment and (b) was anastomosed by a clip of Comparative Example 1.

As shown in FIG. 19, it can be inferred that the expected fastening performance of the clip was maintained since the rats survived even four weeks after liver resection, that is, after severing the blood vessel and bile duct, and X-ray CT did not find generation of a large amount of gas or opening of the clip.

The clip is also expected to finally be degraded and excreted after maintaining its fastening performance for a certain length of time as degradation advances uniformly within the body of the rat. This confirmed the possibility of realizing a safe biodegradable clip.

Figure 20:
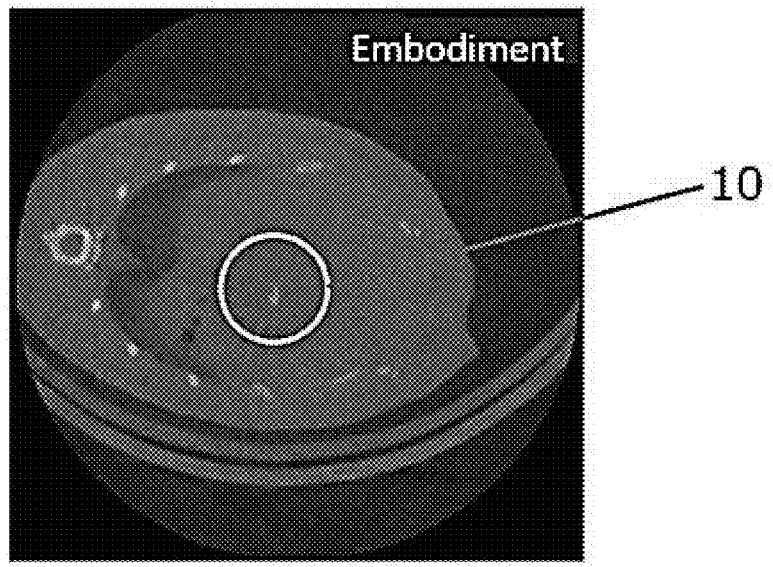
FIG. 20 is reconstructed images 2 of X-ray CT sectional images of a rat (Example 4)
Figure 20:
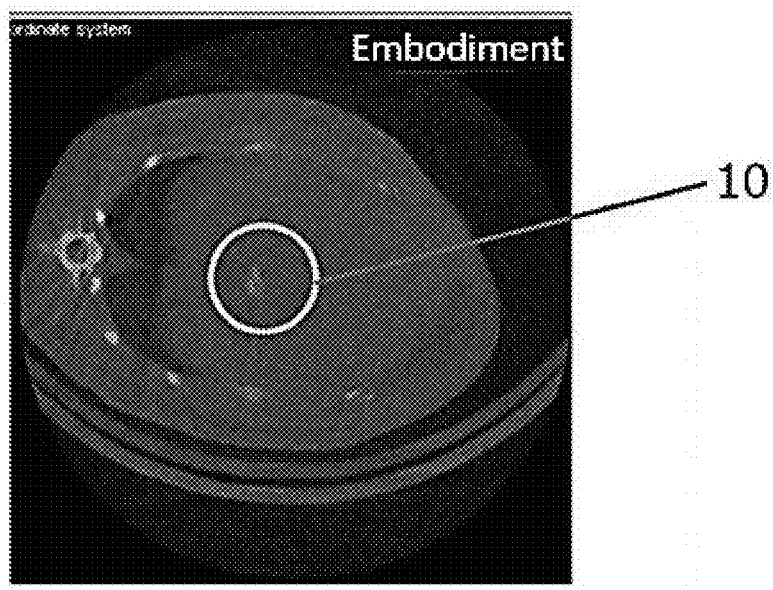

FIG. 20 shows X-ray CT sectional images of a rat. In FIG. 20, (1) is an X-ray CT sectional image from one week after resection and (2) is from four weeks (one month) after resection. FIGS. 20(1) and (2) both show anastomosis by a clip of the embodiment. The clip of the embodiment is understood to be less likely to create metal artifacts during X-ray CT imaging than when a conventional titanium clip is used, and to make it possible to observe the biological tissue clearly without image correction.

INDUSTRIAL APPLICABILITY

The device for fixing biological soft tissue of the present invention is useful in surgical clips, staple, and the like because it can keep tissues joined for the 2-8 weeks it takes biological soft tissue to suture and is excreted after being completely degraded in about one year.

KEY

10: Clip

What is claimed is:

1. A device for fixing biological soft tissue comprising a ternary Mg alloy material of Mg—Ca—Zn, wherein:
    the ternary Mg alloy material contains Ca and Zn within the solid-solubility limit with respect to Mg,
    the remainder comprises Mg and unavoidable impurities,
    a Zn content is more than zero and equal to or less than 0.5 atom %,
    Ca and Zn content levels are such that Ca:Zn=1:x (where x is 1 to 3) by atomic ratio, and
    a crystal grain structure is equiaxed and comprises a plurality of crystal grains having an average crystal grain size of 20 to 250 μm.

2. The device for fixing biological soft tissue according to claim 1, wherein the Zn content is from 0.2 atom % to 0.4 atom %, the Ca and Zn content levels are such that Ca:Zn=1:x (where x is 2 to 3) by atomic ratio.

3. The device for fixing biological soft tissue according to claim 1, wherein:
    crystal grain boundaries of the plurality of crystal grains have crystal misorientation of 15° or greater,
    at least one of the plurality of crystal grains includes crystal subgrains, and
    crystal subgrain boundaries have crystal misorientation of from 3° to less than 15°, which are boundaries that divide the crystal grain structure when a true strain of at least 0.123 is applied by deformation.

4. The device for fixing biological soft tissue according to claim 2, wherein:
    crystal grain boundaries of the plurality of crystal grains have crystal misorientation of 150 or greater,
    at least one of the plurality of crystal grains includes crystal subgrains, and
    crystal subgrain boundaries have crystal misorientation of from 3° to less than 15°, which are boundaries that divide the crystal grain structure when a true strain of at least 0.123 is applied by deformation.

5. The device for fixing biological soft tissue according to claim 1, wherein a biodegradation residual ratio is 50-92% four weeks after implantation and an amount of gas generated in association with degradation is not more than twice a volume of a space formed during bioimplantation.

6. The device for fixing biological soft tissue according to claim 2, wherein a biodegradation residual ratio is 50-92% four weeks after implantation and an amount of gas generated in association with degradation is not more than twice a volume of a space formed during bioimplantation.

7. The device for fixing biological soft tissue according to claim 3, wherein a biodegradation residual ratio is 50-92% four weeks after implantation and an amount of gas generated in association with degradation is not more than twice a volume of a space formed during bioimplantation.

8. The device for fixing biological soft tissue according to claim 4, wherein a biodegradation residual ratio is 50-92% four weeks after implantation and an amount of gas generated in association with degradation is not more than twice a volume of a space formed during bioimplantation.

9. The device for fixing biological soft tissue according to claim 1, wherein the ternary Mg alloy material consists of Mg, Ca and Zn and the unavoidable impurities.

10. The device for fixing biological soft tissue according to claim 1, wherein the device is a surgical clip or staple.

11. The device for fixing biological soft tissue according to claim 10, wherein the surgical clip or staple includes two ends and at least one curved portion disposed between the two ends.

12. The device for fixing biological soft tissue according to claim 1, wherein:
    crystal grain boundaries of the plurality of crystal grains have crystal misorientation of 15° or greater,
    at least one of the plurality of crystal grains includes crystal subgrains, and
    crystal subgrain boundaries have crystal misorientation of from 3° to less than 15°, which are boundaries that divide the crystal grain structure when a true strain of at least 0.193 is applied by deformation.

13. The device for fixing biological soft tissue according to claim 2, wherein:
    crystal grain boundaries of the plurality of crystal grains have crystal misorientation of 15° or greater,
    at least one of the plurality of crystal grains includes crystal subgrains, and
    crystal subgrain boundaries have crystal misorientation of from 3° to less than 15°, which are boundaries that divide the crystal grain structure when a true strain of at least 0.193 is applied by deformation.

* * * * *